United States Patent [19]

Schulte et al.

[11] 4,448,942
[45] May 15, 1984

[54] PROCESS FOR THE PRODUCTION OF HYDANTOINS

[75] Inventors: Bernhard Schulte, Krefeld; Wolfgang Jakob, Moors; Willi Dünwald, Leverkusen; Karl-Heinrichrich Meyer, Krefeld, all of Fed. Rep. of Germany

[73] Assignee: Bayer Aktiengesellschaft, Leverkusen, Fed. Rep. of Germany

[21] Appl. No.: 438,270

[22] Filed: Nov. 1, 1982

[30] Foreign Application Priority Data

Nov. 11, 1981 [DE] Fed. Rep. of Germany ....... 3144701
Nov. 11, 1981 [DE] Fed. Rep. of Germany ....... 3144697

[51] Int. Cl.³ .................... C08G 73/00; C08G 73/06
[52] U.S. Cl. .................................... 525/540; 525/418; 525/451; 525/907; 528/9; 528/266; 528/310; 528/363; 548/308; 548/313
[58] Field of Search ............... 528/363, 310, 266, 9, 528/322; 525/907, 451, 418, 540; 548/313, 308; 526/262

[56] References Cited

U.S. PATENT DOCUMENTS 3,254,036  5/1966  Robinson ..................... 528/363
4,156,074  5/1979  Rottmaier et al. ............ 528/363
4,246,393  1/1981  Zecher et al. ................. 528/75

*Primary Examiner*—Harold D. Anderson
*Attorney, Agent, or Firm*—Connolly and Hutz

[57] ABSTRACT

The invention relates to a new process for the production of compounds containing at least one hydantoin ring by reacting a carbodiimide with a derivative of an α,β-unsaturated carboxylic acid corresponding to the following general formula:

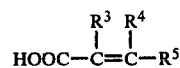

wherein $R^3$, $R^4$ and $R^5$ are as defined in the description.

5 Claims, No Drawings

PROCESS FOR THE PRODUCTION OF HYDANTOINS

This invention relates to a process for the production of compounds containing at least one hydantoin ring in the molecule from carbodiimides and certain derivatives of $\alpha,\beta$-unsaturated carboxylic acids.

Hydantoins, polyhydantoins and processes for the production thereof are known (cf. Am. Chem. J. 45, 383; BE-PS No. 678,282; DE-OS No. 2,714,655).

Low molecular weight hydantoins are preferably used in the pharmaceutical and plant-protection fields, while hydantoins of relatively high molecular weight are of significance, for example, for heat-resistant coating compositions (FR-PS No. 1,484,694).

The present invention relates to a new process for the production of compounds containing hydantoin rings which is characterised in that a carbodiimide is reacted with a derivative of an $\alpha,\beta$-unsaturated carboxylic acid corresponding to the following general formula:

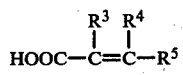

wherein
$R^3$ and $R^4$ independently represent hydrogen or an alkyl radical; and
$R^5$ represents a CN—, CHO—group or a —COOR$^6$— group, or

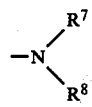

wherein $R^6$, $R^7$ and $R^8$ represent alkyl, cycloalkyl, alkenyl and alkinyl, and temperatures of from $-20°$ to $250°$ C., optionally in the presence of a catalyst and optionally in the presence of a solvent.

It is known [Chem. Rev. 67, 2 (1967), page 107] that the reaction of carbodiimides with carboxylic acids leads to several reaction products, primarily to acyl ureas, carboxylic acid anhydrides and ureas. Thus, the reaction of fumaric acid with carbodiimide to form the corresponding diacyl urea attached through the double bond and the reaction of maleic acid with carbodiimide to form maleic acid anhydride have also been described [J. Prakt. Chem. 79513 (1909)]. F. Zetzsche and G. Röttger even reported detecting $\alpha,\beta$-unsaturated carboxylic acids in the form of ureides by means of carbodiimides [Chem. Ber. 72,1599 (1933)], the N-acyl-N,N'-bis-(4 being formed from di-(4-dimethylaminophenyl)-carbodiimide and a few $\alpha,\beta$-unsaturated carboxylic acids. Hydantoins are not formed in this way.

Surprisingly, hydantoins may be formed by working in accordance with the present invention and using certain derivatives of unsaturated carboxylic acids instead of the carboxylic acids themselves.

According to the present invention, monocarbodiimides containing one —N=C=N— group in the molecule, cyclic dimers or trimers thereof or even linear or branched polycarbodiimides containing more than 2 carbodiimide groups in the molecule may be used as the carbodiimide compounds.

It is preferred to use carbodiimides corresponding to the following general formulae (I) and (II):

wherein
$R^1$ and $R^2$, which may be the same or different, represent an aliphatic radical containing from 1 to 20 carbon atoms, a cycloaliphatic radical containing from 5 to 12 carbon atoms, an aliphatic-aromatic radical containing from 6 to 20 carbon atoms, an aromatic radical containing from 6 to 16 carbon atoms, an aromatic or cycloaliphatic $C_5$-$C_{12}$ radical containing one or more heteroatoms, such as N, O or S, which in either case may optionally be substituted by halogen (chlorine, bromine, iodine or fluorine), nitrile, $C_2$-$C_{12}$ dialkylamino, $C_7$-$C_{12}$ alkyl-arylamino $C_2$-$C_{18}$ alkoxy-carbonyl, $C_7$-$C_{18}$ aroxy-carbonyl, $C_2$-$C_{18}$ alkyl-carboxy, $C_7$-$C_{18}$ aryl-carboxy, $C_1$-$C_{18}$ alkoxy, $C_6$-$C_{18}$ aroxy or diarylamino, $C_1$-$C_{18}$ alkyl, $C_1$-$C_{18}$ halo-alkyl or nitro groups, or a $C_2$-$C_{12}$ dialkylamino, $C_1$-$C_{18}$ alkylamino, $C_2$-$C_{12}$ alkoxy-carbonyl, $C_6$-$C_{18}$ glycosyl radical or an —Si($R^6$)$_3$—, —Sn($R^6$)$_3$—, $SO_2R^6$— group (wherein $R^6$ represents $C_6$-$C_{12}$ aryl or $C_1$-$C_8$ alkyl) or which may be attached to one another as members of corresponding cyclic organic radicals;
Y has the same definition as $R^1$ and $R^2$ and preferably represents aliphatic radicals containing from 2 to 12 carbon atoms, cycloaliphatic radicals containing from 5 to 12 carbon atoms or $C_6$-$C_{16}$ aryl radicals or diphenyl radicals attached through O, S, $SO_2$, $CH_2$, $CH_3$—C—$CH_3$ or CO or —Si($R^6$)$_2$— or Sn($R^6$)$_2$— groups; and
n represents an integer of from 2 to 2000, preferably from 2 to 1000.

According to the present invention, the monocarbodiimides used are N,N'-symmetrically and/or asymmetrically substituted aliphatic, aliphatic-aromatic, cyclic, heterocyclic, aromatic compounds optionally substituted by one or more heteroatoms and containing an —N=C=N— group in the molecule, for example dialkyl carbodiimides, such as dimethyl, diethyl, diisopropyl, dihexyl, dibutyl, dinonyl, didodecyl and distearyl carbodiimide, preferably aromatic, optionally substituted monocarbodiimides, such as diphenyl, ditolyl, dinaphthyl carbodiimide, di-(p-iodophenyl), di-(p-dimethylaminophenyl), di(pyridyl), dinitro, alkoxy, aroxy, chloro, dichloro, trichloro, tetrachloro, pentachloro, benzyl, p-bromophenyl carbodiimide or carbodiimides of dibenzoic acid esters, diphthalic acid esters, diisophthalic acid esters, carbodiimide dibenzonitrile, cycloaliphatic carbodiimides, such as dicyclohexyl carbodiimide, and unsaturated carbodiimides, such as diallyl, dioleyl and dicyclohexenyl carbodiimide.

These carbodiimide compounds may be obtained by known methods, for example from the corresponding thioureas, in the presence of metal oxides, mercury salts, sodium salts, aryl sulphochlorides, or by the oxidation of thioureas or from S-alkylisothioureas, urea compounds as described, for example, in Chem. Rev. 67, 2 (1967), page 107, or from the corresponding isocyanate compounds with elimination of carbon dioxide in the presence of the known catalysts for the elimination of carbon dioxide (FR-PS No. 1,180,307).

In addition, it is possible to use the N-sulphonyl carbodiimides RSO$_2$N=C=NR, the N-aminocarbodiimides RN=C=NR$_2$ or the N,N'-disilyl carbodiimides described, for example in Chem. Rev. 67, 2 (1967), page 107.

Other starting components suitable for use in accordance with the present invention are aliphatic, cycloaliphatic, araliphatic, aromatic and heterocyclic linear or branched polycarbodiimides containing more than 2 carbodiimide groups and mixtures thereof or polycarbodiimides which have a statistical composition or a block-structure comprising different structural elements in a sequence of certain length in the polymer molecule and which may therefore contain the above-mentioned aliphatic, cycloaliphatic, araliphatic, aromatic and heterocyclic structural units in a variety of ratios arranged both in statistical distribution and blockwise in the polymer molecule.

Where the above-mentioned polycarbodiimides containing 2 or more carbodiimide groups in the molecule are synthesised from polyfunctional isocyanates, it is possible to use the catalysts known from the literature (cf. for example FR-PS No. 1,180,307), for example phospholines, phospholidine sulphides etc. or even organometallic compounds of metals of Groups Ia to IIIa, such as phenyl lithium and diethyl zinc.

The polycarbodiimide compounds according to the present invention may be produced from polyisocyanates of the type comprehensively described, for example, in Annalen 562, pages 75 to 136; Am. Chem. J. 45, 383; DE-OS No. 2,714,655; U.S. Pat. No. 3,397,253; EP-PS No. 0 012 379.

It is particularly preferred to use mixtures of polytolylene carbodiimides (2,4- and 2,6-substitution products), poly-m-phenylene carbodiimides and polycarbodiimides based on aniline/formaldehyde condensates having a polyphenylene-methylene structure and poly-4,4'-diphenyl ether, poly-p-phenylene, poly-1,5-naphthylene carbodiimides polyisophorone carbodiimides and polyhexamethylene carbodiimides and/or mixtures thereof and also block polycarbodiimides, for example having the following structures:

—B—B—B—A—A—A—A—B—B—B—

—C—C—B—B—B—A—A—A—A—B—B—B—
C—C— wherein A represents, for example, an aromatic structural element, such as diphenyl methane; B represents an aliphatic radical R, such as the isophorone radical; and C represents an aromatic unit, such as the tolylene or naphthylene group. These block polycarbodiimides may be produced, for example, by successively subjecting the polyfunctional isocyanates individually used to carbodiimide formation in stages. The indicated structures and commercially readily obtainable bifunctional isocyanates demonstrate the range of variation in regard to the sequence lengths of and quantitative ratios between the individual elements. The polycarbodiimides may even be branched, for example in cases where trifunctional and higher isocyanates are used in the carbodiimide-forming reactions.

Suitable derivatives of α,β-unsaturated carboxylic acids correspond to the following general formula:

wherein
R$^3$ and R$^4$ independently hydrogen or an alkyl radical (preferably containing from 1 to 6 carbon atoms); and
R$^5$ represents a CN—, CHO—group, COOR$^6$ or

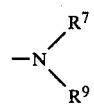

wherein R$^6$, R$^7$ and R$^8$ independently represent
 alkyl (preferably C$_1$–C$_{20}$ such as methyl, ethyl, isopropyl, hexyl, undecyl, eicosyl
 cycloalkyl (preferably C$_5$–C$_{10}$ such as cyclopentyl, cyclohexyl, cycloheptyl, cyclodecyl),
 alkenyl (preferably C$_2$–C$_{20}$ such as allyl, butenyl, pentenyl, decynyl, eicosenyl
 alkinyl (preferably C$_2$–C$_{20}$ such as propargyl, butinyl, pentinyl, hexinyl, octinyl, eicosinyl The following are examples of suitable α,β-unsaturated carboxylic acid derivatives:
 fumaric acid and maleic acid mononitrile, semiamides of fumaric and maleic acids, more particularly N-dimethyl, N-diethyl, N-methylethyl amido maleic acid or amido fumaric acid, monoesters of maleic and fumaric acids, such as fumaric or maleic acid monomethyl ester, monoethyl, ester, which may be obtained by reacting maleic acid, fumaric acid or maleic acid anhydride with the corresponding alcohols or hydroxy ethers, such as alcohols as butanol, isopropanol, hexanol, cyclohexanol, benzyl alcohol, ethylene glycol or ethylene glycol monomethyl ether, allylalcohol, propargylalcohol or undecylalcohol, to form the monoesters β-benzoyl acrylic acid and derivatives thereof, which may be obtained, for example, by Friedel Crafts acylation and β-formyl acrylic acid.

The reaction according to the present invention may be illustrated, for example, by the following equation:

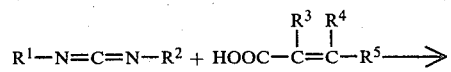

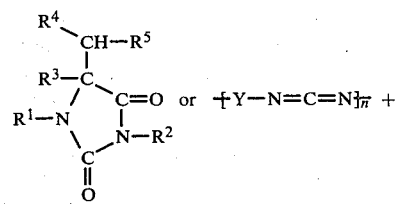

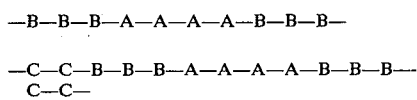

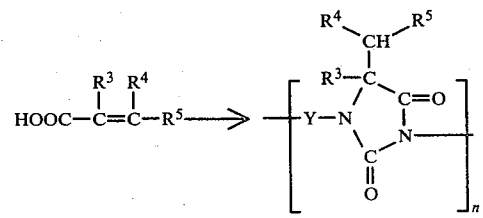

In general, therefore, one equivalent of the α,β-unsaturated carboxylic acid derivative is used per equivalent of carbodiimide, although considerable deviations from these quantitative ratios are also possible.

The hydantoins according to the present invention substituted in the 5-position may be clearly identified by IR-spectra with the aid of the bands characteristic of hydantoins and esters and also by NMR-spectroscopy. The hydantoins of relatively high molecular weight generally have solution viscosities of from 50 to 100,000 mPas, preferably from 100 to 50,000 mPas, as measured on a 15%, by weight, solution in m-cresol 70 at a temperature of 20° C.

The reaction according to the present invention may be carried out in homogeneous phase in which case the solvents do not react under the reaction conditions or form loose, further-reacting addition compounds or in the form of a heterogeneous reaction either as such or in suspension or in an excess of one of the reaction components.

Suitable reaction media are inert organic liquids, for example aliphatic, aromatic or heterocyclic, optionally substituted hydrocarbons, such as chlorinated hydrocarbons, for example carbon tetrachloride, methylene chloride, chloroform, ethylene chloride, tetrachloroethane or cyclohexane, dioxane, tetrahydrofuran, ligroin or chlorobenzene, o-dichlorobenzene, xylene, toluene, carbitol, dimethyl ether, diethyl ether, mixtures of a lower-boiling liquid and a relatively high-boiling liquid, for example mixtures of methylene chloride/chlorobenzene or o-dichlorobenzene or methylene chloride/toluene or xylene, being particularly preferred for the production of compounds containing only one hydantoin ring in the molecule. The more readily volatile component may be utilised for heat dissipation by distillation during the reaction, the reaction by which the hydantoin is formed being completed in the relatively high-boiling component. Hydrocarbons, halogenated hydrocarbons, aromatic hydroxy compounds, such as phenols and cresols, esters, ketones, sulphoxides and sulphones, ethers, substituted amides and nitriles are suitable for use in the production of the polyhydantoins according to the present invention. Examples thereof are xylenes, o-dichlorobenzene, acetophenone, cyclohexanone, propylene carbonate, ε-caprolactam, dimethyl sulphoxide, glycol monomethyl ether acetate, γ-butyrolactone, ε-caprolactone, benzoic acid alkyl esters, N-methyl pyrrolidone, dimethyl formamide, dimethyl acetamide, benzonitrile and mixtures thereof or mixtures with benzyl alcohol.

It is preferred to use binary or, more particularly, ternary mixtures of the above-mentioned solvents or diluents with the compounds just mentioned, such as methylene chloride/toluene or xylene/phenol or cresol or γ-butyrolactone, the most readily volatile component being suitable either for heat dissipation or as an effective solvent for the polycarbodiimides, while the relatively high boiling compound, such as toluene, xylene or "Solvesso," may remain partly or even completely in the lacquer solution on completion of the reaction by which the polyhydantoin is formed so that these components preferably represent diluents commonly used in the field of electrical insulation while the least readily volatile components, such as and phenol, represent the actual solvents for the polyhydantoin reaction product.

Other suitable diluents are aliphatic and aromatic hydrocarbons, such as cyclohexane, xylene, toluene and technical mixtures thereof.

The reaction according to the present invention may be carried out in the presence of catalysts which accelerate the addition of OH-functional compounds to the carbodiimide group, such as copper-I-chloride, copper-II-chloride, or even in the presence of the catalysts suitable for the rearrangement of maleic/fumaric acid, such as iodine, or in the presence of the catalysts known to be suitable for the cyclisation reaction by which the hydantoin ring is formed, such as bases, for example triethylamine, N-methyl morpholine, endoethylene piperazine, acids, for example p-toluene sulphonic acids such as alcohols as methanol, phenol, metals, particularly iron, lead, zinc, tin, copper, cobalt, titanium, manganese, for example titanium tetrabutylate, titanium amino alcohol, iron acetyl acetonate, dibutyl tin laurate, lead acetate, zinc octoate, or in the presence of strong bases, such as potassium t-butylate and sodium methylate.

The catalysts used for forming the carbodiimides, for example phospholine oxide, are particularly suitable.

In most cases, it is not necessary to use a further catalyst.

Where polycarbodiimides produced in known manner from polyfunctional isocyanates are used, the reaction mixture, including the catalyst present therein, may be used directly.

To carry out the process according to the present invention, the carbodiimides, preferably dissolved or suspended in the above-mentioned solvent/diluent combinations, are kept in the above-mentioned reaction media with the α,β-unsaturated carboxylic acids for from a few minutes to several hours at temperatures of from −20° to 250° C., preferably from 30° to 200° C.

The progress of the reaction may be followed by the IR-spectra. In its initial phase, the reaction is highly exothermic, so that the reaction components are preferably combined at low temperatures of from 20° to 50° C., or one of the reaction components is introduced in portions, preferably at from 20° to 45° C. Both the carbodiimides in solution or suspension and also the α,β-unsaturated carboxylic acid derivatives may be initially introduced, optionally in the reaction media mentioned above.

In the production of polyhydantoins on a commercial scale, it is advantageous to produce first the carbodiimide reactant for example from polyfunctional isocyanates because, after the carbodiimides have been produced they may produce the carbodiimide reactant in situ from polyfunctional isocyanates because after they have been produced, the carbodiimides may be immediately further reacted to form the hydantoin according to the present invention.

In cases where the polycarbodiimides used have a block-like structure —B—A—B— (A and B representing sequences of different chain members), a diisocyanate (for example 4,4'-diisocyanatodiphenyl methane) is generally subjected to carbodiimide formation in the above-mentioned solvent or diluent mixture suitable for the production of monohydantoins, of a readily volatile and substantially involatile liquid, such as methylene chloride/toluene, until an almost complete conversion is obtained. Thereafter, the diisocyanate or even, for example, triisocyanate containing the structural unit B (for example isophorone or tolyl) is added, optionally along with more solvent/diluent, and carbodiimide formation continued, in which case monoisocyanates (for example phenyl, tolyl, naphthyl, cyclohexyl, methyl, cyclohexenyl, oleyl isocyanate, isocyanato-benzoic acid esters, phthalic acid esters and isophthalic acid esters) may then be advantageously introduced as regulators as formation of the polycarbodiimide continues.

Thereafter, the α,β-unsaturated carboxylic acid derivatives may be reacted either as such or in solution in the suitable reaction media mentioned above, the highly exothermic nature of the reaction being taken into account. The progress of the reaction to the hydantoin stage is advantageously accomplished by increasing the reaction temperature in stages. It is possible to add inhibitors, such as toluhydroquinone, to prevent polymerisation of the double bond.

The reaction of the polycarbodiimides with α,β-unsaturated carboxylic acid derivatives in accordance with the present invention is preferably carried out in the presence of phenolic compounds, such as phenol, cresol or mixtures thereof, or γ-butyrolactone, N-methyl pyrrolidone or in mixtures of these solvents with benzyl alcohol, the advantage being that these reaction media are also solvents for the polymeric hydantoins.

The reaction is preferably carried out under an inert gas atmosphere, such as nitrogen or argon.

The reaction according to the present invention may be carried out either continuously or in batches under normal pressure or under excess pressure.

The low molecular weight reaction products may be worked-up by the conventional methods, for example by crystallisation.

The monomolecular hydantoins obtainable by the process according to the present invention show activity in the pharmaceutical and plant-protection fields.

The polyhydantoins according to the present invention are distinguished by the particular resistance thereof to high temperatures, by the high solubility thereof and by the excellent levelling properties thereof in wire lacquering and are suitable for the production of adhesives, lacquers, films and mouldings.

The products containing hydantoin groups are particularly suitable for stoving lacquers, particularly wire lacquers and electrical insulation lacquers, in which case the solids content of the possible lacquer solutions may vary within wide limits and is preferably from 20 to 80%, by weight, depending on the particular application envisaged.

In addition, known temperature-resistant plastics and lacquer components, such as polyamides, polyesters, polyurethanes, polyesteramides, polyhydantoins, polyamide imides, polyesterimides, may be modified by hydantoin groups of the type described using the process according to the present invention.

EXAMPLE 1

75 g of 4,4'-diisocyanatodiphenyl methane and 2 g of phenyl isocyanate are dissolved in 70 g of toluene and 70 g of chlorobenzene. Following the addition of 0.5 g of phospholine oxide (a mixture of 1-methyl-1-phospha-2-cyclopentene-1-oxide and 1-methyl-1-phospha-3-cyclopentene-1-oxide), the reaction mixture is heated over a period of 2.5 hours to from 60° to 65° C. (the reaction vessel being connected to a gas meter).

100 g of phenol are added to the polycarbodiimide suspension at 45° C. and a solution of 44 g of maleic acid monomethyl ester (total acid number 422, partial acid number 396) in 60 g of phenol is stirred in at 25° C., the temperature rising to from 75° to 80° C. The reaction mixture is then heated to 180° C. over a period of 4 hours, during which toluene/chlorobenzene distills off. After 30 minutes at 180° C., 40 g of m-cresol 70 are added, followed after another 2 hours by the addition of 35 g of m-cresol 70. After another 30 minutes at 180° C., the reaction mixture is cooled to 140° C. and diluted with 15 g of xylene, giving a clear brown-red polymer solution having a solids content of 31.3% (stoved for 5 minutes at 360° C.) and a viscosity of 1520 mPas (as measured on a 15% solution in m-cresol 70 at 20° C. using a Höppler viscometer. The IR-spectrum of this polyhydantoin ester solution shows the corresponding bands at 1770, 1710 and 1415 cm$^{-1}$. After precipitation of the polymer from CH$_3$OH, the IR-bands typical of hydantoin structures are found at 1770–1775, 1720 and 1410 cm$^{-1}$. (Chlorobenzene may be replaced by xylene in the production of the polycarbodiimide.) Application to a copper wire in the form of a 22% solution (diluted with cresol/xylene in a ratio of 1:1; flowout time from a DIN-4-cup: 470 seconds at room temperature) leads to the following test data (application by spray nozzles; 0.7 mm diameter copper wire), the good levelling properties characteristic of polyhydantoins being observed in conjunction with high softening temperatures.

The lacquered Cu wire stoved at 400° C. in a 4 meter-long oven (wire speed from 8 to 12 meters per minute) is tested in accordance with DIN 46453. It has a softening temperature of at least 350° C., a heat shock of at least 260, high elasticity coupled with edge fibre elongation values of up to 88%, a film hardness of at least 4H (even after 30 minutes in alcohol at 60° C.), long-term heat stability (up to 7 days at 180° C.), a dielectric strength of at least 7 KV and a high resistance to chemicals.

EXAMPLE 2

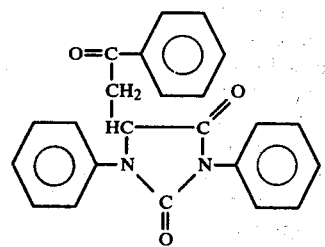

A solution of 17.6 g (0.1 mole) of β-benzoyl acrylic acid in 210 g of toluene is introduced over a period of 1 hour at room temperature into 72 g of a 27% diphenyl carbodiimide solution (0.1 mole) in toluene, followed by stirring for 3 hours. The crystals precipitated are filtered off under suction, washed with toluene and dried (yield 19 g).

5 g of the crystallisate are refluxed for 3 hours in 30 g of o-dichlorobenzene in the presence of small quantities of toluhydroquinone. The reaction mixture is concentrated in vacuo and the residue recrystallised from isopropanol. The white crystallisate (4 g) shows the IR-hydantoin bands at 1770/1710 and 1410 cm$^{-1}$ and the carbonyl band and 1670–1675 cm$^{-1}$. The structure of the 1,3-diphenyl-5-(benzoyl methylene)-hydantoin is confirmed by the NMR-spectrum and by elemental analysis.

| Analysis: $C_{23}H_{18}N_2O_3$ | (370) | | |
|---|---|---|---|
| | C | H | N |
| Calculated | 74.6 | 4.9 | 7.6 |
| Observed | 75.0 | 4.8 | 7.6 |

EXAMPLE 3

50 g of 4,4'-diisocyanatodiphenyl methane and 2.5 g of phenyl isocyanate are dissolved in 40 g of toluene and 40 g of chlorobenzene in a 500 ml three-necked flask (stirrer, internal thermometer, dephlegmator with receiver and a connection to a gas meter). After the addition of 0.5 g of phospholine oxide (a mixture of 1-methyl-1-phospha-2-cyclopentene-1-oxide and 1-methyl-1-phospha-3-cyclopentene-1-oxide), the reaction mixture is heated to 60° C. over a period of 1 hour. The polycarbodiimide suspension obtained shows the IR-bands typical of carbodiimide groups at 2140/2110 cm$^{-1}$, while the isocyanate band may no longer be detected. The reaction mixture is cooled to 40° C. by the addition of 60 g of m-cresol 70. Thereafter, a solution of 27.5 g of maleic acid monomethyl ester in 100 g of cresol is homogeneously stirred in, the temperature rising to approximately 80° C. After the temperature has fallen to 70° C., the carbodiimide is reacted off and the IR-band at 2110-2140 cm$^{-1}$ is no longer observed. The temperature is then increased to 180° C. over a period of 2 hours (during which toluene/chlorobenzene distill off) and, after another 6 hours at from 180° to 185° C., a clear brown-red polymer solution is obtained, having a solids content of 33.1% (2 hours at 200° C.), a viscosity of 750 mPas (as measured on a 15% solution in cresol at 20° C. using a Hoppler viscometer) and the IR-bands typical of hydantoins at 1765, 1710 and 1430 cm$^{-1}$ in m-cresol 70. The application to 0.7 mm diameter copper wire of this lacquer solution diluted with xylene to a solids content of 25% shows the excellent levelling properties characteristic of polyhydantoins and the following measured data:

| Temperature (°C.)/wire speed (m/min.) | 400/10 | 400/11 |
|---|---|---|
| Softening temperature (°C.) | 348 | 330 |
| Heat shock (°C.) | 260 | 260 |
| Pencil hardness | 4 H | 4 H |
| Edge fibre elongation (%) | 67/88 | 67/88 |
| Dielectric strength (kV) | 7.2 | 6.5 |

The tests are carried out in accordance with DIN 46453.

EXAMPLE 4

A solution of 75 g of 4,4'-diisocyanatodiphenyl methane, 3 g of phenyl isocyanate and 1.0 g of phospholine oxide (a mixture of 1-methyl-1-phospha-2-cyclopentene-1-oxide and 1-methyl-1-phospha-3-cyclopentene-1-oxide) in 60 g of toluene and 60 g of chlorobenzene is initially introduced at room temperature into a 500 ml three-necked flask equipped with a stirrer, a dephlegmator, an internal thermometer and a connection to a gas meter. The temperature is then increased to 60° C. over a period of 1 hour, the quantity of gas measured amounting to 8.6 liters. After stirring for 45 minutes at from 55° to 60° C., 100 g of m-cresol 70 are added to the polycarbodiimide suspension obtained (typical IR-bands at 2110/2140 cm$^{-1}$). A solution of 44.5 g of maleic acid monomethyl ester (total acid number 422, partial acid number 396) and 20 mg of iodine in 105 g of m-cresol 70 is stirred into the polycarbodiimide suspension at 40° C. The temperature rises to 76° C. in about 1 minute. After another 5 minutes, the temperature amounts to 67° C. and the carbodiimide band at 2110-2140 cm$^{-1}$ is no longer present in the IR-spectrum. The clear pale yellow viscous reaction solution is heated to 180° C. over a period of 2 hours, during which the toluene/chlorobenzene mixture distills off. After another 8 hours at from 175° to 180° C., a gentle vacuum is briefly applied. The total quantity of distillate amounts to 118 g. 45 g of m-cresol 70 are homogeneously stirred in at 175° C., giving a clear red-brown polyhydantoin solution having a solids content of approximately 28% (stoved for 5 minutes at 360° C.) and a viscosity of 1950 mPas at 20° C. (as measured on a 15% solution in m-cresol 70). After stoving on metal test plates at 360° C., the thus-obtained polyhydantoin solution forms light brown elastic polymer films. The polymer precipitated from methanol shows the bands typical of hydantoins substituted in the 5-position by carbomethoxy groups via methylene bridges at 1770, 1720 and 1410 cm$^{-1}$.

EXAMPLE 5

A solution of 75 g of 4,4'-diisocyanatodiphenyl methane and 2 g of phenyl isocyanate in 60 g of toluene and 80 g of xylene is initially introduced at room temperature. 0.5 g of phospholine oxide (a mixture of 1-methyl-1-phospha-2-cyclopentene-1-oxide and 1-methyl-1-phospha-3-cyclopentene-1-oxide) is added and, with the reaction vessel connected to a gas meter and reflux condenser, the reaction mixture is heated to from 65° to 70° C. over a period of 2 hours, by which time approximately 7 liters of gas have been given off. After the addition of 100 g of m-cresol 70, a solution of 98.5 g of maleic acid monoisopropyl ester in 60 g of m-cresol 70 is added over a period of 1 hour with intensive stirring. After another 100 g of m-cresol 70 and 100 mg of toluhydroquinone have been added, the reaction mixture is heated to 80° C., a clear viscous polymer solution being obtained. The sump temperature is increased to 180° C. over a period of 3 hours during which toluene/xylene distill off. The reaction mixture is then stirred for 6 hours at 180° C., a vacuum being applied towards the end and a total quantity of distillate of approximately 180 g being removed. A clear brown-red polymer solution having a solids content of 32.9% (as determined by stoving for 5 minutes at 360° C.) and a viscosity of 845 mPas (as determined at 20° C. on a solution diluted with m-cresol 70 to a solids content of 15% using a Hoppler viscometer) is obtained and is stoved on metal test plates at 200°, 300° and 360° C. to form clear, elastic lacquer films.

The polymer precipitated from methanol is obtained in the form of a brown-white powder and shows the bands typical of polyhydantoin isopropyl ester at 1775, 1720, 1405 and 1100 cm$^{-1}$.

| Analysis: $(C_{21}H_{20}N_2O_4)_n$ | (364)n | | |
|---|---|---|---|
| | C | H | N |
| Calculated | 69.2 | 5.5 | 7.7 |
| Observed | 69.4 | 5.3 | 7.5 |

A sample of the polyhydantoin is stoved under nitrogen at 300° C. to form a hard moulding.

EXAMPLE 6

A solution of 150 g of 4,4'-diisocyanatodiphenyl methane and 5 g of phenyl isocyanate in 120 g of toluene and 150 g of xylene is initially introduced at room temperature. Following the addition of 1 g of phospholine oxide (a mixture of 1-methyl-1-phospha-2-cyclopentene-1-oxide and 1-methyl-1-phospha-3-cyclopentene-1-oxide), the reaction mixture is heated to 70° C. over a period of 2 hours, the reaction vessel being connected to a gas meter. The carbodiimide solution obtained shows the typical IR-bands at 2110/2140 cm$^{-1}$. Following the addition of 200 g of m-cresol 70, a solution of 78 g (0.6 mole) of maleic acid monomethyl ester in 120 g of m-cresol 70 is introduced over a period of 1 hour at from 35° to 40° C. The temperature is then increased to 60° C. over a period of 45 minutes, resulting in the formation of a clear viscous polymer solution. The solution obtained is heated to 180° C. over a period of 4 hours, during which toluene/xylene distill off. The reaction mixture is then stirred at 180° C. for 4 hours, during which 90 g of phenol are added. Thereafter, a viscous polyhydantoin ester solution is obtained which shows the typical IR-bands at 1770, 1710 and 1410 cm$^{-1}$ and which has a solids content of 30% and a viscosity of 860 mPas (as measured at 20° C. with a Hoppler viscometer after dilution with m-cresol 70 to a solids content of 15%). The stoving of samples of this lacquer solution applied to metal test plates for 5 minutes and 10 minutes at 360° C. gives clear brown-red lacquer films distinguished by the high elasticity thereof.

EXAMPLE 7

88.2 g of a 22% diphenyl carbodiimide solution (0.1 mole) in toluene are added dropwise over a period of 1 hour at room temperature to a solution of 14.4 g (0.1 mole) of fumaric acid monoethyl ester in 80 g of γ-butyrolactone. After stirring for 1 hour at from 30° to 35° C., 50 mg of toluhydroquinone are added and the temperature is increased to 180° C., the toluene distilling off. The mixture is then stirred for 3 hours at that temperature. The reaction solution is then concentrated in vacuo and the reaction product isolated by precipitation from a mixture of water and isopropanol. After drying, 23.6 g of a brown-white solid are obtained which, for further purification, is recrystallised from isopropanol/water and has a melting point of 83° to 85° C. The structure of the 1,3-diphenyl hydantoyl-5-acetic acid ethyl ester is confirmed by IR/NMR-spectra and by elemental analysis.

IR: Hydantoin/ester bands at 1770/1725/1710/1410 cm$^{-1}$

NMR: (CDCl$_3$/DMSO/TMS):

| arom. protons | (10 H) | chem. displacement | 7.0–7.5 ppm |
|---|---|---|---|
| —CH—  | (1 H,t) | chem. displacement | 5.05 ppm |
| —O—CH$_2$— | (2 H,q) | chem. displacement | 3.16 ppm |
| —CH$_2$—CO | (2 H,t) | chem. displacement | 2.95 ppm |
| —CH$_3$ | (3 H,t) | chem. displacement | 1.1 ppm |

Analysis C$_{19}$H$_{18}$N$_2$O$_4$ (338)

| | C | H | N |
|---|---|---|---|
| Calculated | 67.5 | 5.3 | 8.3 |
| Observed | 67.9 | 5.5 | 8.1 |

EXAMPLE 8

225 g of a 19.4% polydiphenyl methane carbodiimide solution in methylene chloride [prepared by the addition of 0.5 g of methyl phospholine oxide to 50 g (0.2 mole) of 4,4'-diisocyanatodiphenyl methane and 3 g (0.025 mole) of phenyl isocyanate in methylene chloride by stirring at reflux temperature (with the reaction vessel connected to a gas meter) until the theoretical quantity of CO$_2$ has been given off; the isocyanate band is no longer observed in the IR-spectrum, instead the typical carbodiimide band is observed at 2140/2110 cm$^{-1}$] is initially introduced at 35° C. After the addition of 100 g of γ-butyrolactone, a solution of 26 g (0.2 mole) of maleic acid monomethyl ester in 10 g of benzyl alcohol and 100 g of γ-butyrolactone is added dropwise over a period of 30 minutes at from 35° to 40° C. After the addition of 100 mg of toluhydroquinone and 20 mg of iodine, the reaction mixture is heated to 180° C. over a period of 4 hours, during which the methylene chloride distills off. The reaction product is then diluted with 50 mg of m-cresol 70. A clear brown-red polymer solution having a solids content of 21.8% and a viscosity of 380 mPas at 20° C. is obtained after 6 hours at from 180° to 185° C. The polymer precipitated and dissolved in and reprecipitated from methanol shows the IR-bands characteristic of hydantoins at 1770–1775/1710–1715 and 1410 cm$^{-1}$. The following proton signals are observed in the NMR (CDCl$_3$/TMS):

| arom. protons | (8 H) | chem. displacement | 7–7.5 ppm |
|---|---|---|---|
| —CH—  | (1 H) | chem. displacement | 4.8 ppm |
|  | (2 H) | chem. displacement | 3.95 ppm |
| —O—CH$_3$ | (3 H) | chem. displacement | 3.55 ppm |
| —CH$_2$— | (2 H) | chem. displacement | 2.97 ppm |

Analysis (C$_{19}$H$_{16}$N$_2$O$_4$)$_n$ (336)$_n$

| | C | H | N |
|---|---|---|---|
| Calculated | 67.9 | 4.8 | 8.3 |
| Observed | 68.2 | 4.8 | 8.1 |

Clear elastic lacquer films are obtained by stoving samples of the lacquer solution obtained on metal test plates for 5 minutes at 360° C.

EXAMPLE 9

A polytolylene carbodiimide solution containing approximately 0.3 mole of carbodiimide groups, prepared from 52.2 g (0.3 mole) of a mixture of 80% of 2,4- and 20% of 2,6-tolylene diisocyanate in 60 g of methylene chloride and 80 g of xylene in the presence of 3.0 g (0.025 mole) of phenyl isocyanate and 0.5 g of methyl phospholine oxide by heating to reflux until the evolution of CO$_2$ stops, is initially introduced.

50 g of phenol and 100 g of m-cresol 70 are introduced at from 40° to 45° C. 43.2 g (0.3 mole) of fumaric acid ethyl ester are then introduced in portions over a period of 30 minutes with cooling. After stirring for 30 minutes at from 40° to 45° C., followed by the addition of 100 mg of toluhydroquinone, the reaction mixture is heated to 180° C. over a period of 3 hours, during which methylene chloride/xylene distills off. The lacquer solution is then stirred for 4 hours at from 180° to 185° C., being diluted with 50 g of phenol as its viscosity increases. A total of 152 g of distillate distills over. 30 g of xylene are homogeneously stirred in at 130° C., giving a clear brown-red polymer solution having a solids content of 29.5% (5 minutes at 360° C.), a viscosity of 870 mPas (as measured at 20° C. on a solution diluted with m-cresol 70 to a solids content of 15%) and the IR-bands characteristic of hydantoins at 1770, 1710 and 1410 cm$^{-1}$. The clear elastic lacquer films stoved onto metal test plates for 5 minutes at 360° C. confirm the high softening temperatures of the polymers containing hydantoin rings.

EXAMPLE 10

A block polycarbodiimide having the structure —B—B—A—A—A—A—B—B— of 50 mole percent of polydiphenyl methane carbodiimide (A) and 50 mole percent of polynaphthylene-1,5-carbodiimide (B), containing approximately 0.4 mole of carbodiimide groups and prepared by subjecting 50 g (0.2 mole) of the diisocyanate of A and 42 g (0.2 mole) of the diisocyanate of B to carbodiimide formation in stages by heating in the presence of 3.6 g (0.03 mole) of phenyl isocyanate and 1 g of methyl phospholine oxide in 200 g of chlorobenzene is initially introduced in the above-mentioned solvent at from 45° to 50° C. Following the addition of 165 g of phenol and 100 g of m-cresol 70, 52 g (0.4 mole) of fumaric acid monomethyl ester are introduced in portions over a period of 45 minutes at from 35° to 40° C. The reaction is exothermic. The reaction mixture is heated to from 180° to 185° C. over a period of 4 hours, during which the chlorobenzene distills off, and is maintained at that temperature for 4 hours. The quantity of distillate removed amounts to 212 g. After cooling to 130° C., 15 g of xylene are homogeneously stirred in, giving a clear viscous polymer solution having the IR-bands characteristic of hydantoin rings at 1770/1710 and at 1410–1415 cm$^{-1}$ and a solids content of 38.2% (5 minutes at 360° C.). Stoving of samples of the lacquer obtained on metal test plates at 360° C. gives clear brown-yellow elastic lacquer films which confirms the high softening temperatures of these polymers containing hydantoin rings. A solution diluted with m-cresol 70 to a solids content of 15% has a viscosity of 1365 mPas at 20° C.

EXAMPLE 11

100 mg of diazabicyclooctane and 15 g of phenol are introduced at room temperature with approximately 10 ml of toluene into a solution of 200 g (0.8 mole) of 4,4'-diisocyanatodiphenyl methane in 200 g of methylene chloride and 200 g of xylene. After stirring for about 20 minutes at from 40° to 45° C., 1.5 g of methyl phospholine oxide are introduced and the reaction mixture is heated to reflux with the reaction vessel connected to a gas meter. The mixture is then stirred at from 50° to 55° C. until 16.8 liters of $CO_2$ have been given off. The polycarbodiimide solution then shows the IR-absorption bands characteristic of carbodiimide groups at 2135/2105 cm$^{-1}$. After cooling to 40° C., 300 g of phenol and then 49.8 g (0.125 mole) of N,N'-bis-(2-methoxy-2-carbonyl)-4,4'-diaminodiphenyl methane are added over a period of 15 minutes at from 40° to 45° C. A solution of 24.5 g (0.65 mole) of maleic acid monomethyl ester in 100 g of phenol is then introduced over a period 30 minutes with cooling, another 10 g of toluene being added for rinsing purposes. After another 15 minutes at from 40° to 45° C., the carbodiimide group may no longer be observed in the IR-spectrum.

The reaction mixture is then heated to 140° C. over a period of about 1 hour, during which solvent distills off. After stirring for 1.5 hours at from 145° to 150° C., the mixture is heated for 2 hours to 170° C. and then stirred for 1 hour at from 170° to 175° C., 200 g of cresol being introduced as the viscosity increases and a total of 380 g of distillate being removed. A clear brown-red polymer solution having the IR-bands characteristic of hydantoins at 1765/1705 and 1415 cm$^{-1}$ is obtained. The solution has a solids content of 30.5% (stoved for 5 minutes at 360° C.) and a viscosity (as measured at 20° C. on a solution diluted with m-cresol 70 to a solids content of 15%) of 2300 mPas.

EXAMPLES

Comparison Example A 250 g of 4,4-diisocyanato-diphenyl methane, 6 g of phenyl isocyanate and 1.5 g of methyl phospholine oxide (a mixture of 1-methyl-1-phospha-2- and 1-methyl-1-phospha-3-cyclopenten-1-oxide) are introduced at room temperature into 250 g of chlorobenzene and 250 g of toluene. The condensation reaction by which the carbodiimide is formed is accompanied by the evolution of $CO_2$. The temperature is increased to 50° C. during the reaction. When the evolution of gas ceases, 50 g of phenol and 130 g of maleic acid monomethyl ester are introduced at 50° C. A highly viscous mass which may no longer be stirred is obtained.

Where 250 g of trichloroethylene are used instead of chlorobenzene, a gelatinous mass which, once again, may no longer be stirred is precipitated after addition of the maleic acid monomethyl ester.

EXAMPLE 12

1500 g of 4,4'-diisocyanato-diphenyl methane and 36 g of phenyl isocyanate are condensed at from 40° to 50° C. in 1500 g of methylene chloride and 1500 g of toluene in the presence of 9 g of methyl phospholine oxide as catalyst until no more carbon dioxide is given off, resulting in formation of the polycarbondiimide. 330 g of phenol are then introduced at 45° C., followed by the introduction with cooling of 780 g of maleic acid monomethyl ester. After stirring for 1 hour at from 45° to 50° C., 1740 g of a mixture of equal parts of phenol and a technical cresol mixture are added and the temperature is increased to 180° C. over a period of about 3 hours during which the methylene chloride and the toluene distill off. Another 2070 g of the phenol/cresol mixture are then introduced, followed by stirring for 4 hours at 180° C. The polyhydantoin is obtained in the form of an approximately 33% solution which shows a viscosity $\eta^{25}$ of 17400 mPas and the IR spectrum bands characteristic of hydantoins at 1715 and 1775 cm$^{-1}$.

In order to carry out wire lacquering tests, the polyhydantoin is diluted to a solids content of 27% using a mixture of equal parts of cresol and xylene, giving a viscosity equivalent to 230 seconds (23° C.).

A 0.7 mm diameter wire is lacquered in a vertically arranged lacquering installation comprising a 3 meters long radiation oven.
Lacquering conditions:
Oven temperature: 400° C.
Number of passages: 6
Method of application: spray nozzles
Graduation of nozzles: 0.74, 0.76, 0.76, 0.78 0.78, 0.80
Lacquering speed: 14 meters per minute
Properties of the lacquered wired obtained (DIN 46 453) Increase in diamter through lacquering: 58–60 μm
Heat shock (1×diameter): 260° C.
Softening temperature: 380°–390° C.
Pencil hardness: 4–5H
Pencil hardness after 30 minutes in contact with ethanol (23° C.): 4–5H

EXAMPLE 13

A solution of the polycarbodiimide is produced as described in Example 1 from 250 g of 4,4'-diisocyanatodiphenyl-methane and 3 g of phenyl isocyanate in 250 g of methylene chloride and 250 g of toluene using methyl phospholine oxide (1.6 g) as catalyst. Phenol and a solution of 158 g of fumaric acid monoisopropyl ester in 50 g of toluene/methylene chloride (1:1) are then introduced at 50° C. After stirring for 1 hour at 50° C., 1 g of N,N-bis-(dimethylaminoethyl)-methylamine and 320 g of phenol/cresol (1:1) are added. The temperature of the reaction mixture is then increased to 180° C. over a period of 4 hours, during which the methylene chloride and the toluene distill off. Another 370 g of phenol/cresol (1:1) are then added, followed by stirring for 4 hours at 180° C.

An approximately 33% solution of the polyhydantoin isopropyl ester having a viscosity of 16,560 mPas and the bands characteristic of hydantoins at 1710 and 1760 cm$^{-1}$ is obtained.

A sample of the lacquer solution is applied to a copper wire and stoved in the same way as described in Example 1. For a lacquering speed of 14 meters per minute, the maximum edge fibre elongation amounts to 88%, the heat shock to 260° C. and the softening temperature to 400° C.

EXAMPLE 14

Following the addition of 0.5 g of triethylene diamine, a solution of 130 g of maleic acid monomethyl ester in 125 g of methylene chloride is introduced with cooling at from 10° to 20° C. into a solution of a polycarbodiimide of 250 g of 4,4'-diisocyanatodiphenylmethane, 6 g of phenyl isocyanate and 1.5 g of methyl phospholine oxide in 625 g of methylene chloride. After stirring for 30 minutes at 20° C., 50 g of phenol are added, the temperature is increased to 50° C. and 290 g of phenol/cresol (1:1) are introduced. The reaction mixture is then heated to 180° C., the methylene chloride distilling off, after which 340 g of phenol/cresol (1:1) are added and the reaction completed over a period of 4 hours at 180° C. The polyhydantoin methyl ester is obtained in the form of a clear brown solution having a viscosity $\eta^{25}$ of 10,800 mPas. A sample of the lacquer solution is coated onto a glass plate and stoved for 15 minutes at 200° C. and then for 15 minutes at 300° C. to form a clear, elastic lacquer film.

EXAMPLE 15

A polycarbodiimide solution of 250 g of 4,4'-diisocyanatodiphenyl methane and 1.5 g of methyl phospholine oxide in 500 g of methylene chloride is introduced at 50° C. into a solution of 147 g of maleic acid monomethyl ester in 300 g of methylene chloride and 50 g of phenol. After stirring for 1 hour at 50° C. 290 g of phenol/cresol (1:1) are added, the temperature is increased to 180° C., the methylene chloride distilling off, and another 240 g of phenol/cresol are added. A solution of the polyhydantoin methyl ester having a viscosity $\eta^{25}$ of 5300 mPas and hydantoin bands at 1710 and 1770 cm$^{-1}$ is obtained after 4 hours at 180° C.

A sample of the hydantoin solution is coated onto a metal test plate and stoved first at 200° C. and then at 300° C. to form a clear elastic lacquer film.

EXAMPLE 16

130 g of maleic acid monomethyl ester are added dropwise with cooling at from 45° to 50° C. to a polycarbodiimide solution of 250 g of 4,4'-diisocyanatodiphenyl methane, 6 g of phenyl isocyanate and 1.5 g of methyl phospholine oxide in 250 g of methylene chloride, 250 g of toluene and 57 g of caprolactam. After stirring for 30 minutes at the above-mentioned temperature of from 45° to 50° C., 50 g of phenol are added and, after another 30 minutes, 290 g of phenol/cresol (1:1) are introduced. The temperature is then increased to 180° C. over a period of 4 hours, during which the methylene chloride and toluene distill off, 340 g of phenol/cresol are introduced and the reaction mixture stirred for 4 hours at 180° C. The polyhydantoin methyl ester is obtained in the form of an approximately 33% brown solution having a viscosity $\eta^{25}$ of 11,500 mPas.

A sample of the lacquer solution is coated onto a glass plate and stoved at 200° C. and then at 300° C. to form a clear elastic lacquer film.

EXAMPLE 17

12 g of methanol are added dropwise to a solution of a carbodiimide of 250 g of 4,4'-diisocyanato-diphenyl methane, 6 g of phenyl isocyanate and 1.5 g of methyl phospholine oxide in 250 g of methylene chloride and 250 g of toluene, after which the solution is maintained at 50° C. for 2 hours. Following the addition of 50 g of phenol, 130 g of maleic acid monomethyl ester are introduced with cooling at 45° C., followed by stirring for 1 hour at 50° C. 290 g of phenol/cresol are then introduced, after which the reaction mixture is heated to 180° C., the methylene chloride and toluene distilling off, another 340 g of phenol/cresol (1:1) are added and condensation completed over a period of 4 hours at 180° C. A 33% polyhydantoin methyl ester solution having a viscosity $\eta^{25}$ of 7020 mPas is obtained.

A sample of the lacquer solution is applied to a glass plate and stoved first at 200° C. and then at 300° C. to form a clear elastic lacquer film.

EXAMPLE 18

A solution of 206 g of maleic acid monobenzyl ester in 100 g of methylene chloride is added dropwise at 45° C. to a polycarbodiimide solution of 250 g of 4,4'-diisocyanato-diphenyl methane, 3 g of phenyl isocyanate and 1.5 g of methyl phospholine oxide in 250 g of methylene chloride, 250 g of toluene and 50 g of phenol. After stirring for 30 minutes at the above-mentioned temperature of 45° C., 310 g of phenol/cresol (1:1) are added and the temperature is increased to 180° C. over a period of 1.5 hours. 360 g of phenol/cresol are then added and the reaction mixture stirred for 4 hours at 180° C., giving a 33% solution of the polyhydantoin benzyl ester having a viscosity $\eta^{25}$ of 6200 mPas.

A sample of the lacquer solution is applied to a metal test plate and stoved first at 200° C. and then at 300° C. to form a clear elastic lacquer film.

We claim:

1. A process for the production of a compound having at least one hydantoin ring, wherein a polyimide is reacted with an acid corresponding to the formula $$\underset{\text{HOOC}-\overset{R^3}{\underset{|}{C}}=\overset{R^4}{\underset{|}{C}}-R^5}{}$$

wherein

R³ and R⁴ represent hydrogen or an alkyl radical;

R⁵ represents a CN— group, a CHO— group, COOR⁶— group or

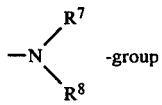

in which R⁶, R⁷ and R⁸ represent alkyl, cycloalkyl, alkenyl or alkinyl; at temperatures of from about −20° to 250° C.

2. A process according to claim 1 wherein the reaction preceeds in contact with a solvent and a catalyst.

3. A process according to claim 2 wherein the solvent is methylenechloride or a mixture of solvents containing methylenechloride.

4. A process according to claim 1 wherein the polyimide is a linear or branched polycarbodiimide.

5. A process as claimed in claim 1 wherein said polyimide is of the formula $$\{Y-N=C=N\}_n.$$

wherein

Y represents at least one aliphatic radical containing 2 to 12 carbon atoms, cycloaliphatic radical containing from 5 to 12 carbon atoms or C₆–C₁₆ aryl radical or diphenyl radical attached through O, S, SO₂, CH₂, CH₃—C—CH₃ or CO or —Si(R⁶)₂— or Sn(R⁶)₂— group; and n represents an integer of from 2 to 2000.

* * * * *

UNITED STATES PATENT AND TRADEMARK OFFICE
CERTIFICATE OF CORRECTION

PATENT NO. : 4,448,942
DATED : May 15, 1984
INVENTOR(S) : Schulte et al

It is certified that error appears in the above-identified patent and that said Letters Patent is hereby corrected as shown below:

In item [75] in the first column of the front page, change the third inventor's name from "Karl-Heinrichrich Meyer" to -- Karl-Heinrich Meyer --.

Signed and Sealed this

Twenty-sixth Day of February 1985

[SEAL]

Attest:

DONALD J. QUIGG

Attesting Officer

Acting Commissioner of Patents and Trademarks